(12) United States Patent
Chenaux

(10) Patent No.: US 8,475,466 B2
(45) Date of Patent: *Jul. 2, 2013

(54) CALIBRATED MECHANICAL ORTHOPEDIC DRIVER WITH WEAR-COMPENSATED TORQUE-LIMITING MECHANISM

(75) Inventor: Fabrice Chenaux, West Chester, PA (US)

(73) Assignee: Greatbatch Medical S.A., Orvin (CH)

( * ) Notice: Subject to any disclaimer, the term of this patent is extended or adjusted under 35 U.S.C. 154(b) by 735 days.

This patent is subject to a terminal disclaimer.

(21) Appl. No.: 11/958,447

(22) Filed: Dec. 18, 2007

(65) Prior Publication Data

US 2011/0184425 A1 Jul. 28, 2011

Related U.S. Application Data

(60) Provisional application No. 60/870,455, filed on Dec. 18, 2006.

(51) Int. Cl.
*A61B 17/56* (2006.01)

(52) U.S. Cl.
USPC .......................................................... 606/104

(58) Field of Classification Search
USPC .......................................................... 606/208
See application file for complete search history.

(56) References Cited

U.S. PATENT DOCUMENTS

| | | | | |
|---|---|---|---|---|
| 4,915,672 A | * | 4/1990 | Girguis | 464/145 |
| 5,174,424 A | * | 12/1992 | Eriksson | 192/56.61 |
| 5,195,624 A | * | 3/1993 | Eriksson | 192/56.2 |
| 5,531,461 A | * | 7/1996 | Huff et al. | 279/62 |
| 5,690,577 A | * | 11/1997 | Enzmann et al. | 475/265 |
| 5,797,309 A | * | 8/1998 | Eberhart | 91/375 A |
| 5,814,097 A | * | 9/1998 | Sterman et al. | 623/2.11 |
| 6,033,334 A | * | 3/2000 | Showalter | 475/206 |
| 6,270,436 B1 | * | 8/2001 | Reik et al. | 474/8 |
| 6,640,674 B1 | * | 11/2003 | Rinner et al. | 81/475 |
| 7,001,333 B2 | * | 2/2006 | Hamel et al. | 600/242 |
| 7,243,581 B1 | * | 7/2007 | Gao | 81/473 |
| 7,272,998 B1 | * | 9/2007 | Gauthier | 81/473 |
| 7,976,464 B2 | * | 7/2011 | Shluzas et al. | 600/219 |
| 2004/0194460 A1 | * | 10/2004 | Ito et al. | 60/487 |
| 2005/0137052 A1 | * | 6/2005 | Miller et al. | 476/38 |
| 2005/0148826 A1 | * | 7/2005 | Paolitto et al. | 600/232 |
| 2010/0179560 A1 | * | 7/2010 | Chenaux | 606/104 |
| 2011/0184425 A1 | * | 7/2011 | Cheraux | 606/104 |

FOREIGN PATENT DOCUMENTS

EP 1110512 * 6/2001

* cited by examiner

*Primary Examiner* — Bruce E Snow
*Assistant Examiner* — Melissa Hoban
(74) *Attorney, Agent, or Firm* — Michael F. Scalise

(57) ABSTRACT

A torque-limiting driver for orthopedic surgical use is described. The torque-limiting driver has a housing to which a torque force may be applied and transferred to a driver output shaft. The housing encloses a cam bearing assembly having a ball cage disposed so that balls of the ball cage move along a first vector path (Vr) radial to the axis of rotation. The bearing assembly also has an inner race abutting the ball. The inner race travels along a second vector path (F) parallel to the axis of rotation. The first vector path (Vr) and the second vector path (F) are not co-axial. A bearing load assembly applies a bias force (F) to the inner race of the cam bearing assembly to set the calibrated maximum amount of torque that can be transmitted via the housing through the cam bearing assembly to the output shaft of the torque-limiting driver.

23 Claims, 7 Drawing Sheets

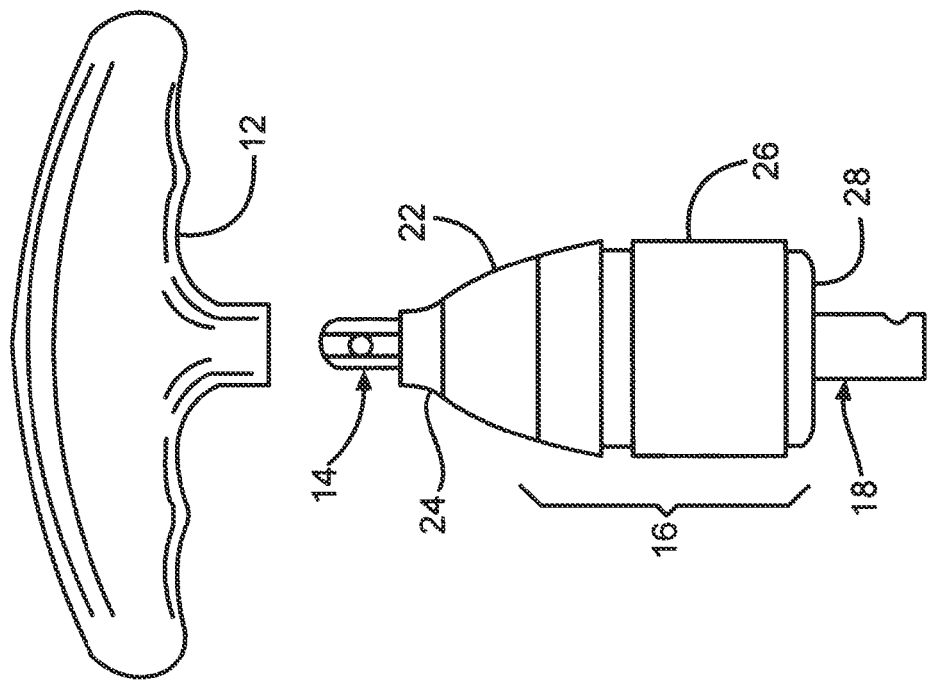
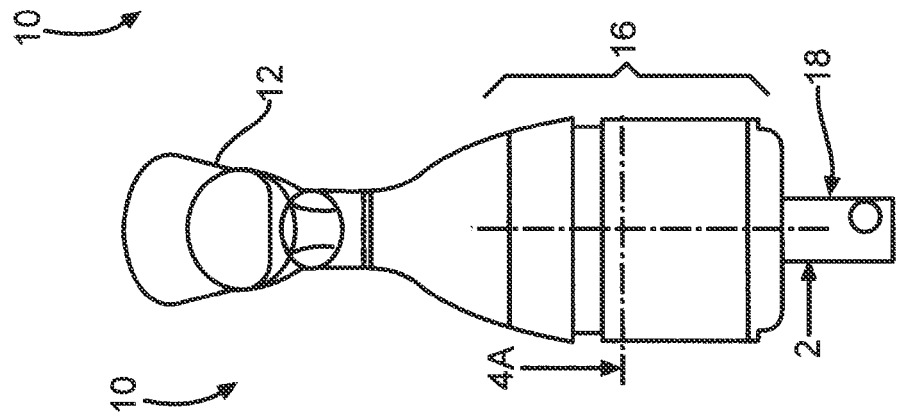

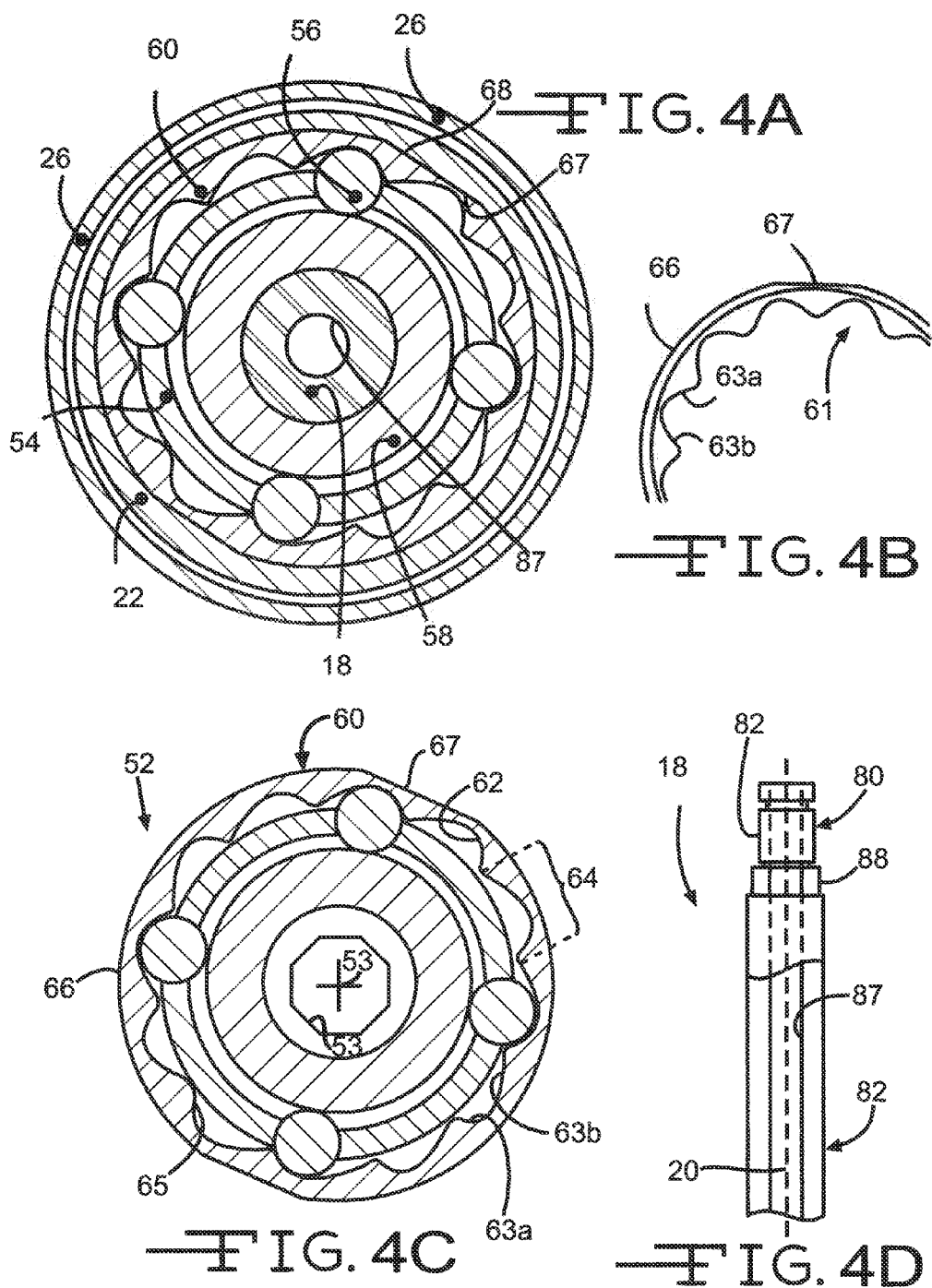

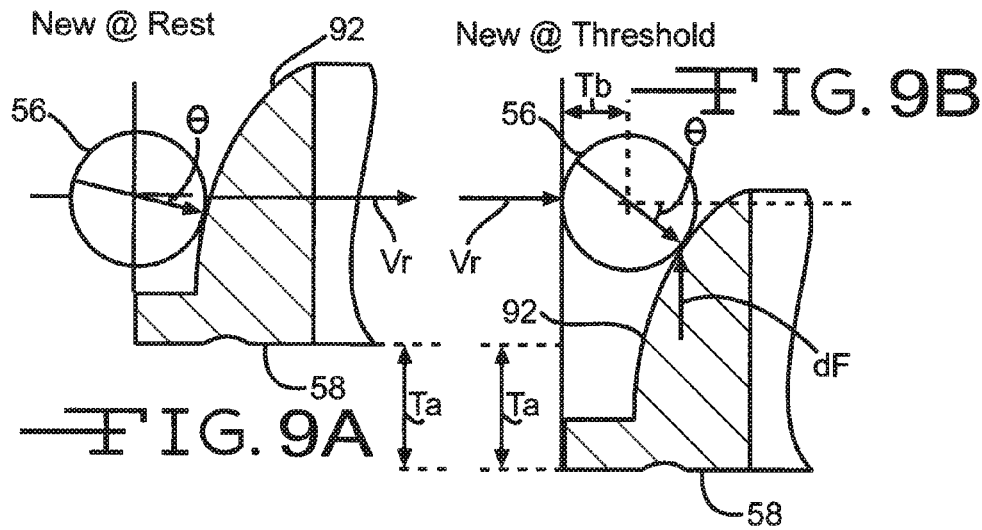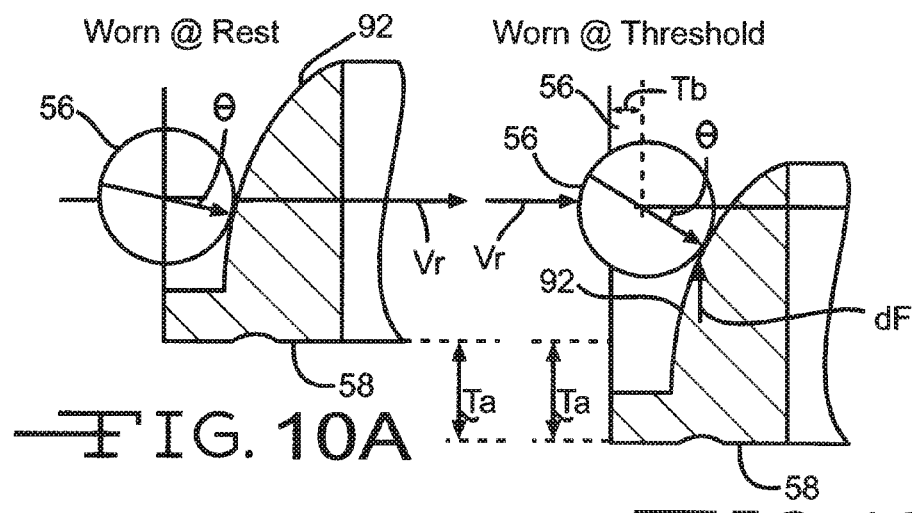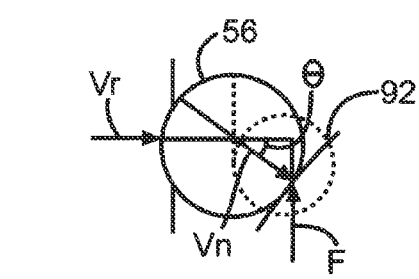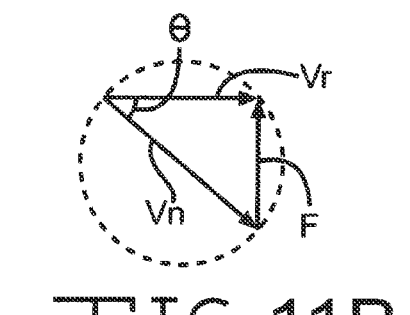

CALIBRATED MECHANICAL ORTHOPEDIC DRIVER WITH WEAR-COMPENSATED TORQUE-LIMITING MECHANISM

CROSS-REFERENCE TO RELATED APPLICATION

The present application claims the benefit of prior filed U.S. Provisional Application Ser. No. 60/870,455, filed on 18 Dec. 2006, which is incorporated herein by reference.

FIELD OF THE INVENTION

The present invention is in the field of orthopedic surgical instrumentation (believed to be classified in US class 606/53). Specifically, the present invention relates to surgical instrumentation for use in bone preparation for the manipulation, placement or removal of an internal bone prosthesis (believed to be classified in US class 606/53; 86). More specifically, the present invention relates to a screw or pin placement or removal means particularly adapted for use in an orthopedic environment for inserting or extracting an elongated element having helical threads (believed to be classified in US class 606/53; 86; 104).

BACKGROUND OF THE INVENTION

When a mechanical fastener driver is used to insert or to remove a threaded fastener, rotational force or torque is applied to the fastener to cause it to rotate. In this manner, the fastener can be driven into or removed from a work piece. In the orthopedic surgical arts, the work piece is usually bone. There exist in the orthopedic surgical arts applications in which threaded fasteners are inserted into and removed from bone. As in other fields, there exists the need in some of these applications to control the torque applied via the driver to the fastener. For example in the orthopedic surgical arts, it is common for a threaded fastener to be driven into a human bone. A universal problem in the field is that when the torque applied to the driver is too great, the bone at the work site may be permanently damaged by the fastener. Also, where one surgeon may successfully drive the screw into the work site, a different surgeon or the same surgeon on a different occasion may apply too great a force to the fastener, damaging the bone. Additionally, in some surgical procedures, if the fasteners are set with insufficient torque, this can result in a bad outcome as well.

Thus, there is a continuing need in the orthopedic surgical field for mechanical drivers adapted for specific surgical applications in which the torque transmitted via the driver to the orthopedic fastener is controlled such that different operators of the driver cannot exceed a predetermined torque when using a driver for that application. The field has been motivated to address this need and torque-limiting drivers are available for orthopedic use.

However, a continuing problem in the industry is that, although the calibration of such instruments can be accurately set during their production, once in use in the field, their repeated use, cleaning and sterilization (heat and chemical) gradually alters the calibration setting of these instruments and shortens their useful service life. It would be beneficial in the orthopedic surgery industry to have available an alternative calibrated torque-limiting fastener driver adapted for orthopedic surgical use that has an extended accurate calibration service life.

SUMMARY OF THE INVENTION

The present invention is a calibrated mechanical torque-limiting driver for orthopedic surgical use. The present torque limiting-driver has a wear-compensated torque-limiting mechanism that substantially increases the durability of the pre-set torque calibration beyond other currently available orthopedic torque-limiting drivers. The driver limits the maximum amount of rotational force, or torque, transferable to the device's driver output shaft. In keeping with its orthopedic instrument features and limitations, the driver is adapted to permit its cleaning and sterilization between uses. The present mechanical torque-limiting orthopedic fastener driver comprises a housing assembled of at least two main parts: a first proximal (the user) housing section and a second distal housing section, which also serves as a torque setting cap. The first proximal housing section has a drive end at which a drive interface is disposed. In a preferred embodiment, the driver interface is attached to a manual T-handle. The second housing section has a distal shaft end with a shaft port through which the driver output shaft of the driver device extends. The first and the second housing sections are mechanically linked with each other via a coupling that fastens the housing sections together.

The wear compensating, torque-limiting assembly of the driver is disposed within the housing. The torque limiting assembly mechanically connects the housing and drive interface with the driver output shaft. The torque-limiting assembly is finely adjustable to selectively set the maximum amount of torque that can be transmitted via the drive interface of the housing to the driver output shaft. This is accomplished via a torque adjustment mechanism portion of the torque-limiting assembly. The driver output shaft has a housing end received and freely rotatable in the first housing section. A shank portion of the driver output shaft is in communication with the torque-limiter assembly, and rotatable depending on the amount of torque being applied to the housing. The output shaft extends from a shaft port at the distal shaft end of the second housing section. The driver output shaft has a distal fastener interface end adapted to engage an orthopedic fastener, such as a bone screw or an extension device. Because there are many different configurations of orthopedic fasteners, the fastener interface end can be set up to accept an adaptor which mates with a specific configuration of fastener, or alternatively, because the output shaft itself is easily removable and replaceable, different output shafts can be provided which have their distal fastener interface end specifically adapted for use with a desired fastener.

The coupling means for joining the housing components can be accomplished by any of a variety of means know to and selectable by one of skill in the art, so long as the means allows disassembly and reassembly of the housing sections to provide access to the torque-limiting assembly. Additionally, the torque-limiting assembly is adapted to provide for cleaning and sterilization between uses.

In particular, the torque-limiting assembly of the present driver addresses the need in the orthopedic surgical industry for a calibrated torque-limiting fastener driver, wherein the calibrated maximum torque setting remains appropriately correct despite the expected wear of bearing surfaces and change in the physical constants of biasing components, in order to extend the accurate calibration service life of the instrument.

The torque-limiting assembly was designed to easily and finely set the calibration of the torque limitation of the present device, and the assembly cooperates with the housing coupling to provide this feature in the present driver. However, an unexpected result of the design of the torque-limiting assembly is that the service life expectancy of the calibration setting is substantially increased. This unexpected result addresses a continuing problem in the industry in that, although the calibration of an orthopedic driver can be accurately set during production, once in use in the field, repeated use, cleaning and sterilization (heat and chemical) gradually alter the calibration setting of the instrument and shorten its useful service life.

There are three main component features of an orthopedic mechanical torque-limiting device that are subject to wear and that can consequently cause loss of calibration over time from repeated usage and sterilization. These are: the two main load bearing surface contact interfaces, and the biasing mechanism. Although there are other points of wear in the device, these are the ones that typically have the greatest influence on loss of calibration. More specifically, these component features are: (1) the point load interface between each of the main bearing balls and the outer bearing race; (2) the point load interface between the main bearing balls and the inner bearing race; and (3) the counter-torque bias spring. The first two are surface-to-surface wear problems. The third problem is a change in spring tension (the normal bias force) exhibited by the bias spring due to normal use, and also in part due to the effect of repeated sterilization of the device, especially heat sterilization. The wear-compensating design of the present torque-limiting assembly solves this problem by distributing one of the points of wear over a very much larger contact surface, and by using the other point of wear to alter a force vector to compensate for change in the Hook's constant (or its equivalent) of the bias spring. The specifics of wear-compensation mechanism will be detailed below.

The torque-limiting assembly includes a bias mechanism, which applies a loading force to a dome-shaped inner bearing race. The shaped inner race transmits pressure to a set of departured ball bearings disposed in an outer cam race with a lobulated race profile/surface. The cage of the departured balls is fixed to the output shaft of the driver. When torque is applied to the driver interface, the balls tend to engage the detent lobes on the race surface of the profiled cam race and rotate with the cam, thus rotating the cage and attached driver output shaft. Sufficient torque causes the balls to roll up the slope of the detent lobes. When the balls pass the high point of the detent lobes on the cam race, the cam race slips (the balls advance to the adjacent detent lobe) relative to the cage and rotation is not imparted to the driver output shaft. The maximum torque of the torque-limiting driver may be controlled by adjusting the second housing cap of the device. The relationship between the structure and function of these elements and features are made clear to one of ordinary skill in the art in view of the detailed description below and the drawings contained herein.

BRIEF DESCRIPTION OF THE DRAWINGS

FIGS. 1A and 1B are side and front plan views of a torque-limiting orthopedic fastener driver of the present invention.

FIG. 4A is a cross-sectional view taken through torque limiter and housing of the fastener driver along the plane indicated in FIG. 1A.

FIG. 4B is a top plan view of a portion of an outer cam race exemplifying an inner cam surface having symmetric cam lobes.

FIG. 4C is a cross-sectional view of an example of a cam bearing assembly taken along the plane indicated in FIG. 1A.

FIG. 4D is a partial cross-sectional view of a proximal portion of the driver output shaft of the present orthopedic fastener driver.

FIGS. 9A and 9B are cross-sectional views taken through a portion of the cam bearing assembly showing the relationship of the ball bearing to the inner race when the assembly is new and the lobes of the cam race (not shown) are unworn.

FIGS. 10A and 10B are cross-sectional views taken through a portion of the cam bearing assembly showing the relationship of the ball bearing to the inner race when the assembly is worn and the lobes of the cam race (not shown) are worn.

FIGS. 11A and 11B are schematic drawings illustrating the mathematical relationship of the force vectors at play in the present wear compensated torque-limiting driver.

DETAILED DESCRIPTION OF THE INVENTION

Figure 2:
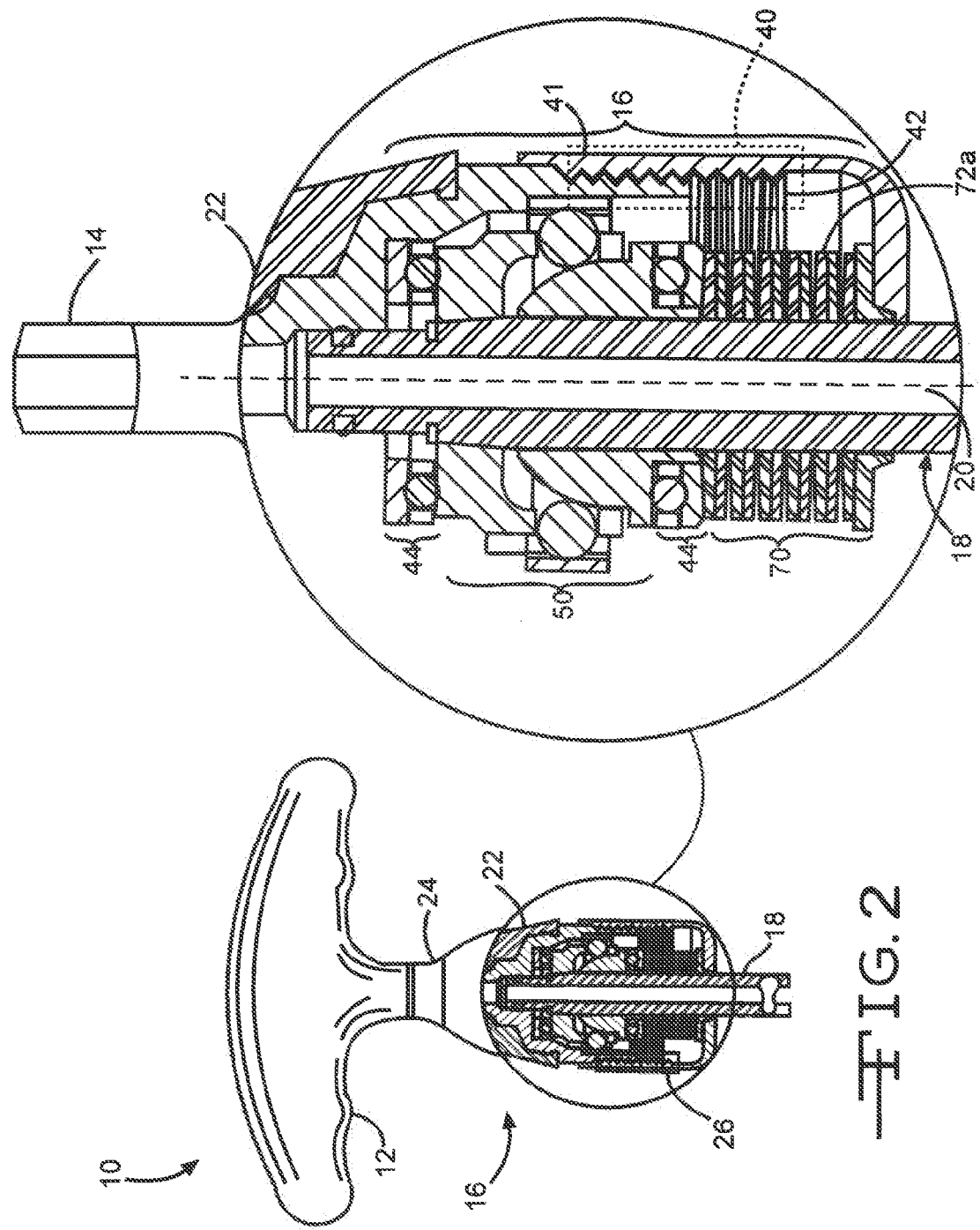
FIG. 2 is a front plan with enlarged partial cross-sectional view of an embodiment of the present orthopedic fastener driver.

Referring now to the drawings, the details of preferred embodiments of the present invention are graphically and schematically illustrated. Like elements in the drawings are represented by like numbers, and any similar elements are represented by like numbers with a different lower case letter suffix. In the following detailed description, reference is made to the accompanying drawings, which show by way of illustration specific embodiments in which the invention may be practiced. However, it is to be understood that other embodiments will become apparent to those of ordinary skill in the art upon reading this disclosure. The following detailed description is, therefore, not to be construed in a limiting sense, as the scope of the present invention is defined by the claims.

As illustrated in FIGS. 1A and 1B, the present invention is a wear compensated torque-limiting driver 10 suitable for orthopedic surgical use. The driver 10 comprises a housing 16 to which a torque force may be applied, for example, via a manually operated T-handle 12. As shown in FIG. 2, the housing 16 encloses a torque limiting assembly 50 including a cam bearing mechanism 52 having a ball cage 54 and ball bearings 56. The ball cage 54 is disposed so that at least one ball bearing 56 of the ball cage 54 moves along a first radial direction or path Vr perpendicular to the axis of rotation 20 of the driver 10 due to a torque applied to the housing. An inner bearing race 58 abuts the at least one ball bearing 56, which inner race 58 travels along a second direction or path Tr while abutting the at least one ball bearing 56. The first direction Vr and the second Tr are not co-axial. In the embodiment exemplified in the drawings, the first Vr and second Tr directions are at a right angle to each other. A bearing load assembly 70 is in mechanical communication with the cam bearing assembly 52 and applies a normal bias force F to the inner race 58 of the cam bearing mechanism 52. In the preferred embodiment, this bias is selectively set during production of the driver to set the calibrated maximum amount of torque that can be transmitted via the housing 16 through the cam bearing assembly 52 to a driver output shaft 18 of the torque-limiting driver 10. The driver 10 is adapted to enable its cleaning and sterilization for orthopedic surgical use.

Figures 3A, 3B:
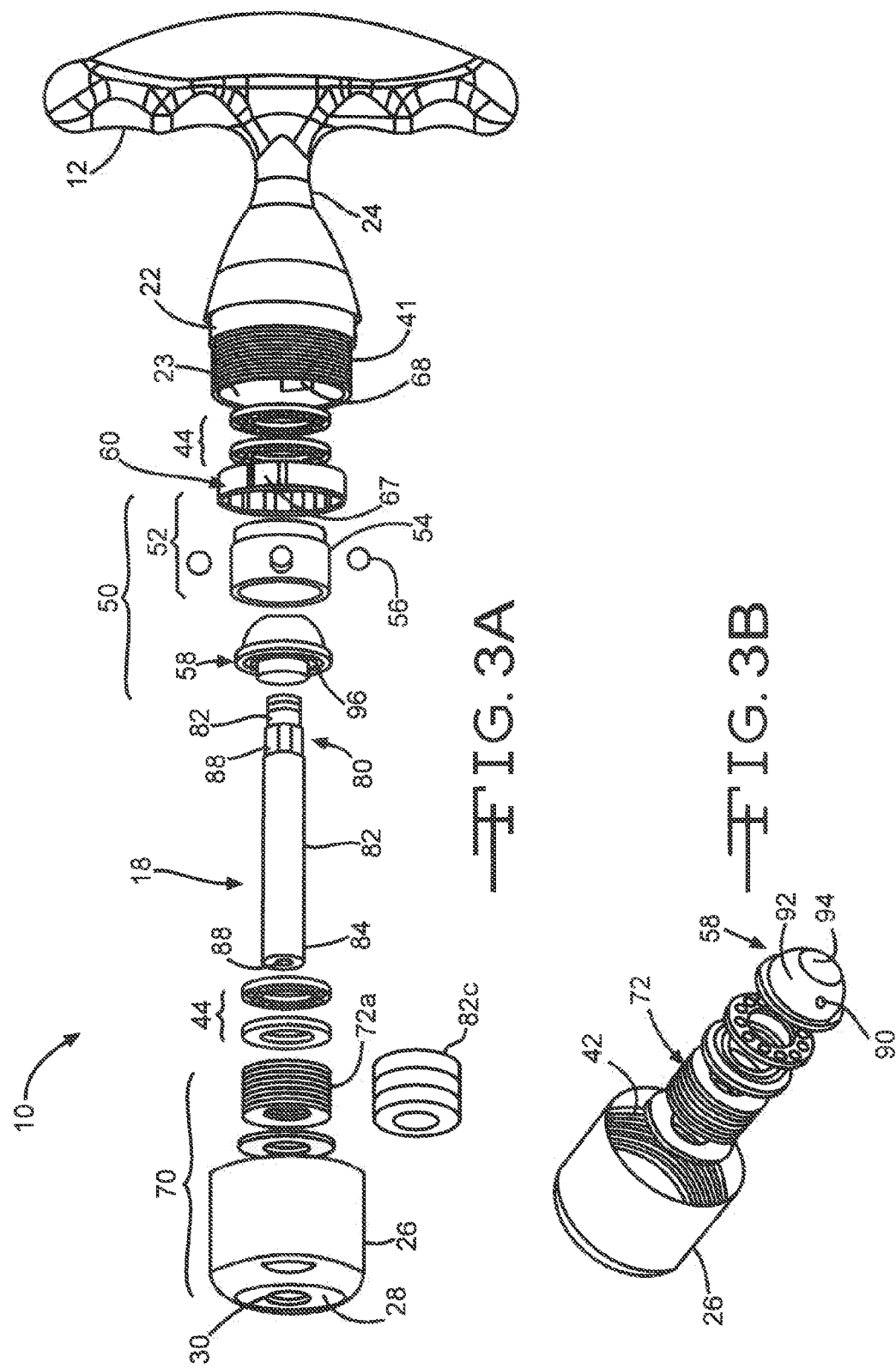
FIGS. 3A and 3B are exploded views showing the relationship of the major components of the present orthopedic fastener driver.

The present wear-compensated, calibrated mechanical torque-limiting orthopedic fastener driver 10 is adapted for surgical use. It can also be subjected to the sterilization processes typical for such instruments in the field. As illustrated in FIGS. 3A and 3B, the driver 10 comprises a housing 16 having a first proximal housing section 22 with a drive end 24, at which a drive interface 14 is disposed. A second housing section 26 mechanically communicates with the first housing section 22 by a housing coupling 40. In the embodiment illustrated, the housing coupling 40 comprises complementary threaded interfaces 41, 42 on the first and the second housing sections 22, 26 of the housing 16. More specifically, the housing coupling 40 comprised an externally threaded interface 41 on the first housing section 22 of the housing 16, and a complementary internally threaded interface 42 on the second housing section 26. The second housing section 26 has a distal shaft end 28 with a shaft port 30 through which the driver output shaft 18 projects along the rotation axis 20 of the fastener driver 10. FIG. 4A is a cross-sectional view taken through torque limiter and housing of the fastener driver 10 along the plane indicated in FIG. 1A and illustrates the relationships of the housing sections 22, 26 to the cam bearing assembly components 56, 58, 60 and the output shaft 18.

Figure 6:
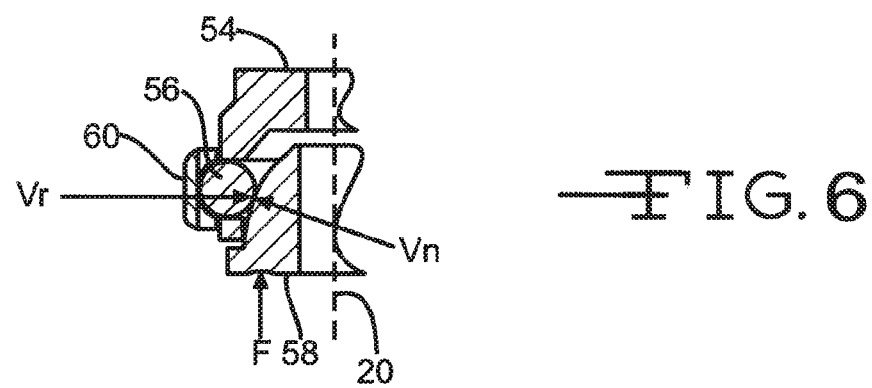
FIG. 6 is a cross-sectional view taken through the torque-limiting assembly of the fastener driver taken from the enlarged portion of FIG. 2.

A wear-compensated torque-limiting assembly 50 is disposed within the housing 16. The wear-compensated torque-limiting assembly 50 is mechanically adapted to apply torque from the drive interface 14 to the driver output shaft 18. This is accomplished via a cam bearing assembly 52 which converts rotational force on the housing 16 into a radial force vector Vr on the ball bearings 56 of the cam bearing assembly 52. For reference, see FIG. 4C and FIG. 6. The torque-limiting assembly 50 in combination with the bearing load assembly 70 provides for selectively setting a maximum amount of torque that can be transmitted by the drive interface 14 of the housing 16 to the driver output shaft 18. The bearing load assembly 70 is in mechanical communication with the torque-Limiting assembly 50, and applies a normal bias force F thereto to selectively set the amount of rotational force on the housing 16 that can translate into the calibrated maximum amount of radial force vector Vr and that can be transmitted via the torque limiting assembly to the driver output shaft 18.

Figure 4E:
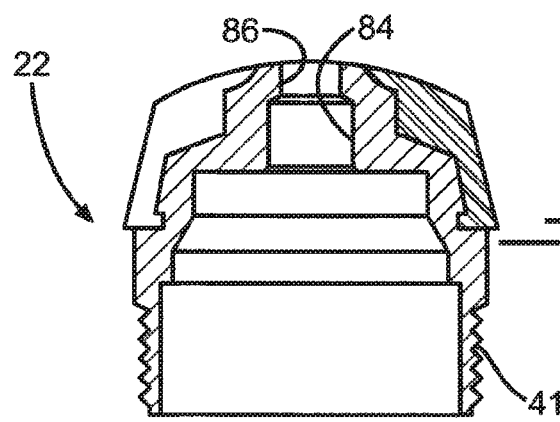
FIG. 4E is a cross-sectional view of the first/proximal drive end housing taken from the enlarged portion of FIG. 2.

The driver output shaft 18 has a proximal housing end 80 (FIG. 4D) passing through the torque-limiter assembly 50, which is received along the axis of rotation 20 in rotatable communication within the proximal housing section 22. As shown in FIGS. 4D and 4E, this is accomplished in the illustrated embodiments by the drive end 24 of the first housing section 22 being adapted to have a pilot bearing receiver 84 disposed inside the drive end housing section 22 concentric to the rotation axis 20. The pilot hearing receiver 84 closely receives the shaft pilot bearing 82 of the driver output shaft 18. Optionally, the pilot bearing receiver 84 disposed inside the drive end housing section 22 communicates with a housing cannula 86 disposed concentric to the rotation axis 20 through the drive end 24 of the first housing section 22.

Preferably, as illustrated in the drawings, a thrust bearing assembly 44 is disposed in front of the pilot bearing receiver 84 concentric to the rotation axis 20, through which the shaft pilot 82 of driver output shaft 18 passes to enter the pilot bearing receiver 84. The thrust bearing assembly 44 is in rotating communication with the ball cage 54 of the cam bearing assembly 52. The driver output shaft 18 optionally has a central shaft cannula 87. When the output shaft 18 is received by the pilot bearing receiver 84, the housing cannula 86 is coaxially aligned with the shaft cannula 87. The output shaft 18 also has a driver shank portion 82, which extends through the shaft port 30 of the second housing section 26. The distal shaft end 84 of the output shaft 18 is adapted to terminate in a fastener, interface 88 for engaging a fastener, an extension rod or other tool head (not shown).

The wear-compensated torque-limiting assembly 50 comprises a cam bearing assembly 52 (FIG. 4C) having a ball cage 54 and a plurality of ball bearings 56 held in a departured relationship to each other by the ball cage 54. The cam bearing assembly 52 has an outer cam race 60 in which the ball bearings 56 of the ball cage 54 are received. An inner wear-dispersing ball loading race 58 is received, in turn, within the ball cage 54. The outer cam race 60 is held in a fixed non-rotating condition relative to the housing 16. This is accomplished in the embodiments illustrated by a cam retainer interface 67 on an outer surface 66 of the outer cam race 60 received in a complementary cam retainer interface 68 on an inner surface 23 of the first housing section 22. For reference, see FIGS. 4A to 4C. The ball cage 54 is held in a fixed non-rotating condition relative to the driver output shaft 18 by the keyed cam assembly bore 53 concentric with the rotation axis 20. The keyed cam assembly bore 53 of the ball cage 54 is adapted to engage a complementary keyed (or asymmetric) interface 88 at the housing end 80 of the driver output shaft 18. For reference, see FIGS. 4C and 4D. The mating of the complementary keyed interfaces 53 and 88 prevents rotation of a ball cage 54 of the cam bearing assembly 52 relative to the driver output shaft 18.

Figure 7A:
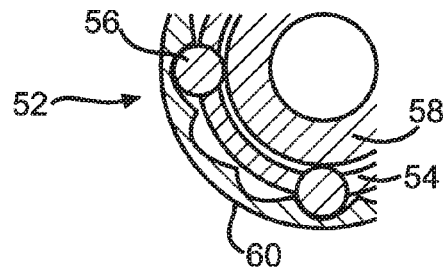
FIGS. 7A-7C are cross-sectional views taken through different portions of the fastener driver in a normal condition: (A) cam bearing assembly taken from FIG. 4A, (B) the torque limiting assembly, the bearing load assembly and output shaft taken from the enlarged portion of FIG. 2, and (C) the torque-limiting assembly taken from FIG. 6.
Figure 8A:
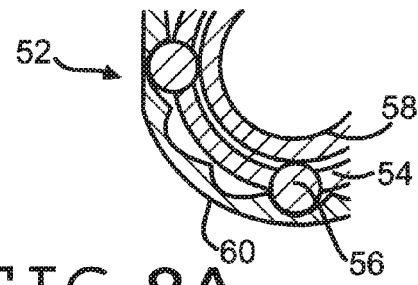
FIGS. 8A-8C are cross-sectional views taken through different portions of the fastener driver in a torque-loaded condition: (A) cam bearing assembly taken from FIG. 4A, (B) the torque-limiting assembly, the bearing load assembly and output shaft taken from the enlarged portion of FIG. 2, and (C) the torque-limiting assembly taken from FIG. 6.
Figure 7B:
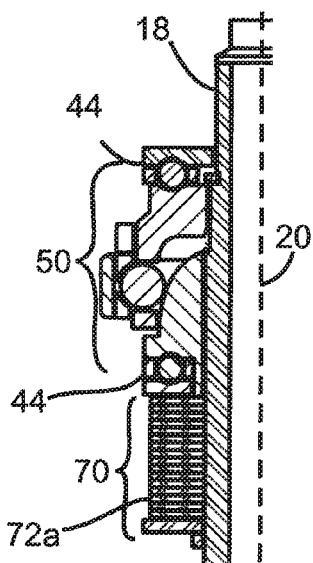
Figure 8B:
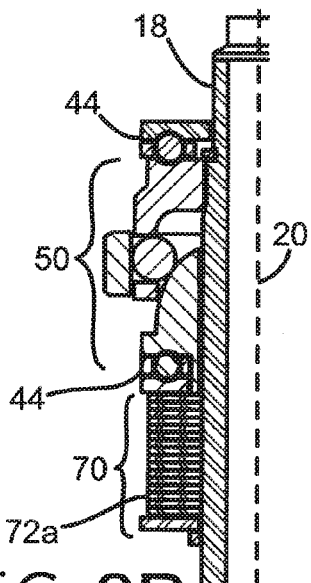
Figure 7C:
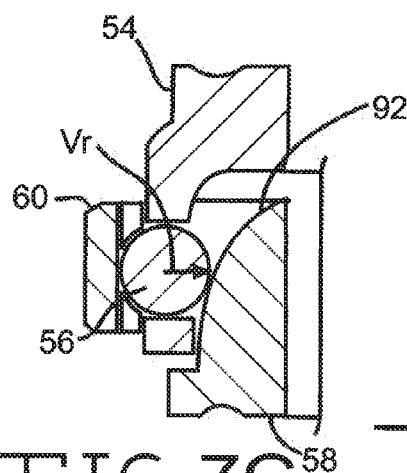
Figure 8C:
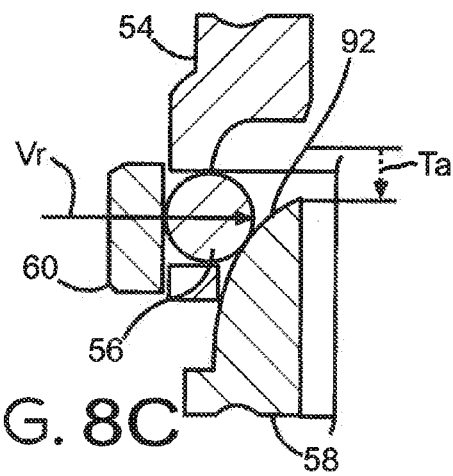

The cam race 60 and the inner race 58 are both in mechanical communication with the ball bearings 56. The outer cam race 60 is in mechanical communication with the ball bearings 56 and moves them in a direction along a direction vector Vr substantially along a radius of the rotation axis 20 of the fastener driver 10. The inner bearing loading race 58 is in mechanical communication with the ball bearings 56 and is moved by them in a non-radial direction substantially parallel to the rotation axis 20 and in the direction of the bias force vector F (when torque is applied to the cam race 60 via the housing section 22). The resultant non-radial force vector Vn of the combined movement directions is at an angle θ relative to the direction vector Vr. For reference, see FIG. 6. FIGS. 7A-7C are cross-sectional views taken through different portions of the fastener driver 10 in a normal (no torque applied) condition: (A) cam bearing assembly taken from FIG. 4A, (B) the torque-limiting assembly, the bearing load assembly and output shaft taken from the enlarged portion of FIG. 2, and (C) the torque-limiting assembly taken from FIG. 6. FIGS. 8A-8C are cross-sectional views taken through the same portions of the fastener driver 10, but in a torque-loaded condition. What these figures illustrate is that in response to sufficient torque being applied to the cam race 60 of the cam bearing assembly 52, the ball bearings 56 are forced to move along a radius of the rotation axis 20 in direction Vr. The ball bearings 56 move radially to the rotation axis 20. Movement of the ball bearings 56 applies a force against the wear dispersing surface 92 of the inner race 58 causing it to travel a distance Ta along the rotational axis 20 against the bias force F. The axial travel distance Ta of the inner race 58 is determined by the difference in the force exerted by the ball 56 against the race surface 92 and the bias force F on the inner race 58. This difference in force dF is equivalent: to the resultant non-radial vector force Vn. (For support, see FIGS. 11A and 11B). As shown in FIGS. 9A and 9B, when the cam bearing assembly is new or the lobes 64 of the cam race 60 are unworn, the radial distance the ball 56 must travel (the throw of the ball) Tb to reach the threshold of the lobe 65 is at a maximum. For reference, see also FIG. 5A. However, as shown in FIGS. 10A and 10B, as the lobes 64 wear, the radial distance Tb the ball 56 must travel to reach the threshold of the lobe 65 gets smaller. For reference, see also FIG. 5B.

The outer cam race 60 has an inner race surface 61 in mechanical contact with the ball bearings 56. The inner surface 61 is adapted with a plurality of cam lobes 64 disposed to provide that each ball bearing 56 is similarly accommodated in a lobe 64. There can be fewer ball bearings 56 in the ball cage 54 than there are lobes 64 in the inner race surface 61. Each lobe 64 has a bottom ball detent portion 62, two ramp portions 63a and 63b and a cam lobe high-point portion 65. A ball throw distance Tb is defined as the distance between the bottom ball detent portion 62 and the cam high-point portion 65 of the lobe 64 along a radius of the rotation axis 20.

The inner ball loading race 58 has a dome shaped portion 90 (FIG. 3B) with a wear-dispersing outer surface 92. A central bushing 94 runs through the inner race 58 perpendicular to a base 96 of the dome shape portion 90 and concentric with the rotation axis 20 of the driver 10. This bushing 94 is slidable over the shank 82 of the output shaft 18 along the rotation axis 20. The dome shaped outer surface 92 forms the angle θ between a radius of the rotation axis 20 and a ball radius perpendicular to a point of contact of the ball bearing 56 with the outer surface 92. The angle θ increases at a rate dependent on the curvature of the outer surface 92 as an axial displacement Ta increases. A specific advantage of the dome shaped outer surface 92 of the inner wear-dispersing ball loading race 58 is that it presents a substantially larger contact surface for mechanical contact with the ball bearings 56, and consequently disperses wear from the ball bearings 56 over a substantially larger contact surface than with a conventional bearing race.

The bearing load assembly 70 has a mechanism to provide a normal bias force to the inner race 58, preferably through a thrust bearing assembly 44. In the preferred embodiment illustrated, the bearing load assembly 70 utilizes a set of Belleville washers to accomplish the bias mechanism 72. However, one of skill in the art could select and practice other biasing mechanisms in the present invention, such as: a coil spring 72a, a set of Belleville washers 72b, a gradient e.g., gas piston compression device, and a compression resistant material 72c in mechanical communication with the wear-compensated torque-limiting assembly 50.

The outer cam race 60 of the mechanical torque-limiting assembly 50 has an inner race surface 61 adapted with a plurality of cam lobes 64. In one preferred embodiment, the inner race surface 61 has an asymmetrical profile, which preferentially limits rotation of the driver output shaft 18 to a single direction, e.g., clockwise. For reference, see FIGS. 4A and 4C. The asymmetry lies in one slope 63a of the lobe 64 being shorter than the other slope 63b. Alternatively, the inner surface 61 of the cam race 60 can be adapted with a plurality of cam lobes 64 having a symmetrical profile to enable rotation of the driver output shaft 18 in a first clockwise direction and a second counter-clockwise direction, and the symmetrical profile limits the predetermined torque equally in both directions of rotation. For reference, see FIG. 4B. In this case, the symmetry lies in both slopes 63a, 63b of the lobe 64 being the same.

Figure 5A:
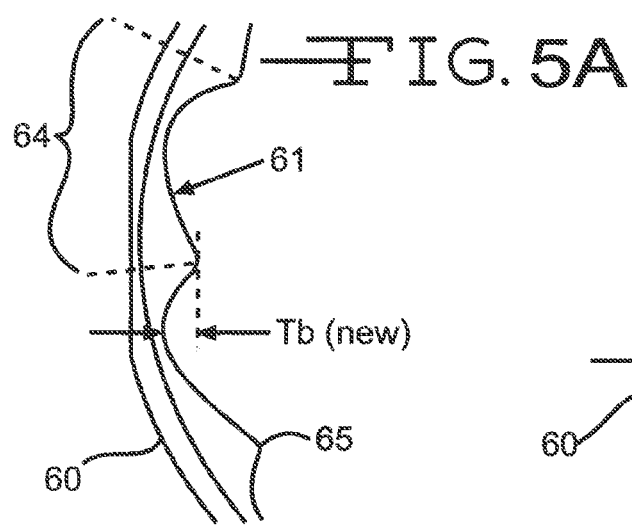
FIGS. 5A and 5B are top plan views of a portion of an outer cam race exemplifying an inner cam surface having asymmetric cam lobes, and showing (A) new or unworn lobes and (B) worn lobes.
Figure 5B:
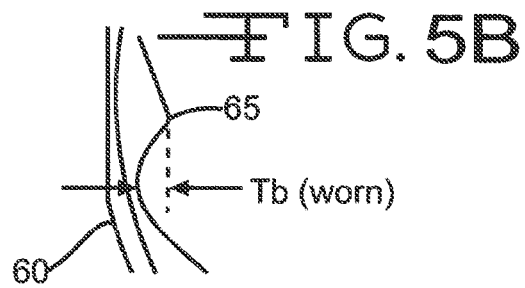

As shown in FIGS. 5A and 5B, the lobes 64 of the outer cam race 60 are subject to wear, particularly, the cam lobe high-point portion 65. As the cam lobe high-point portion 65 wears, the ball throw distance Tb decreases. For reference, see and compare FIG. 5A to FIG. 5B. This is one of the points of wear in the instrument 10 that is a potential source of de-calibration.

An example of the wear-compensated torque-limiting feature of the present driver 10 is as follows read in conjunction with FIGS. 11A and 11B.

EXAMPLE 1

At the outset, it is noted that the sine of an angle is as follows: sin A=a/c, sin B=b/c. The cosine of an angle is as follows: cos A=b/c, cos B=a/c. The tangent of as angles is as follows: tan A=a/b, tan B=b/a.

Assume $\theta=30°$ and Vr=100 units when instrument is new.
A. New Cam Race and New Spring
   cos θ=Vr/Vn
   Vn=100 units/0.866=115 units
   sin θ=F/115 units
   F=0.500×115 units=58 units
   Therefore, in this system: 58 units of Bias force (F) equal 100 units of Torque force (Vr)
B. Effect of Worn Spring
   Assume Bias force (F) reduced by 10%.
   F=52 units
   What is the equivalent torque force (Vr)?
   Tan θ=F/Vr
   VR=52 units/0.577=90
C. However: Effect of Worn Cam Race Lobe
   Assume $\theta=27°$ due to cam wear
   Assume Bias force (F) reduced by 10%: F=52 units
   What is the equivalent Torque force (Vr)?
   Tan 27'=F/Vr
   Vr=52 units/0.510=102 units
   Therefore, in this scenario, a 10% reduction in Bias force (F) and a 10% reduction in θ due to cam lobe wear do not substantially alter calibration of the torque (Vr) of the instrument.

In an advantage, the torque-limiting driver 10 may be used in an application in which precision torquing operations are performed. As one example, the torque-limiting driver 10 may be used in surgical operations in which screws are driven into a bone, such as during orthopedic operations and the like. By controlling the torque applied to the screw, the torque-limiting driver 100 ensures that, no matter which surgeon drives the screw into the bone, the screw will be driven at a predetermined torque.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

The invention claimed is:
1. A torque-limiting fastener driver, which comprises:
   a) a housing comprising a proximal housing section having a drive end at which a drive interface is disposed, and a distal housing section connected to the proximal housing section by a housing coupling, wherein the distal housing section has a shaft port into which a driver output shaft is detachably insertable to extend along a rotation axis of the fastener driver;
b) a torque-limiting assembly disposed within the housing, the torque-limiting assembly comprising:
  i) a cam bearing assembly comprising at least two ball bearings held in a departured relationship to each other by a ball cage, and
  ii) an outer cam race in which the ball bearings are received, wherein the outer cam race has an inner race surface provided with a plurality of repeating asymmetric cam lobes, each asymmetric cam lobe comprising a cam high point spaced from a bottom ball detent portion intermediate opposed ramp portions of a lesser and a greater pitch, and
  iii) an inner race comprising a dome-shaped outer surface aligned symmetrically along the rotation axis,
  iv) wherein the outer cam race contacts each ball bearing received in a lobe at a radial vector (Vr) that is aligned substantially along a radius perpendicular to the rotation axis of the fastener driver, and the outer surface of the inner race contacts each ball bearing at a non-radial vector off-set by an angle from the radial vector; and
c) a bearing load assembly providing a bias force (F) against the torque-limiting assembly, wherein the bias force is adjustable to selectively set a maximum amount of torque that is transmittable via the drive interface to the driver output shaft that is detachably insertable into the shaft port at the distal section of the housing,
d) wherein in a rest position of the driver, the ball bearings reside in the bottom ball detent portion of a first cam lobe of the outer cam race and in contact with the inner race, and
e) wherein with the driver output shaft received in the shaft port at the distal housing section, the drive end of the proximal housing section is manipulatable to impart a torque force that causes the inner race to rotate about the rotation axis as the ball bearings contacting the outer cam race at the radial vector move up the lesser pitch ramp of one of the plurality of asymmetric cam lobes while contacting the outer surface of the inner race at the non-radial vector to thereby axially displace the inner race in a first direction along the rotation axis until the ball bearings crest at the cam high point and fall along the greater pitch ramp into the bottom ball detent portion of a next one of the plurality of asymmetric cam lobes with the inner race then moving in a second, opposite direction along the rotation axis back to the rest position.

2. The driver of claim 1 wherein the housing coupling comprises complementary threaded interfaces on the proximal and distal housing sections.

3. The driver of claim 1 wherein the housing coupling comprises a first externally threaded interface on the proximal housing section and a complementary internally threaded interface on the distal housing section.

4. The driver of claim 1 wherein the drive end of the proximal housing section has a pilot bearing receiver disposed therein that is concentric with the rotation axis, the pilot bearing receiver being sized to receive a shaft pilot of the driver output shaft.

5. The driver of claim 4 wherein the pilot bearing receiver includes a housing cannula that is concentric with the rotation axis of the drive end of the proximal housing section.

6. The driver of claim 4 wherein a thrust bearing assembly disposed distal to the pilot bearing receiver and concentric to the rotation axis is rotatable with the ball cage of the cam bearing assembly, and wherein the shaft pilot of the driver output shaft which is detachably insertable into the shaft port of the distal housing section passes through the pilot bearing receiver.

7. The driver of claim 1 wherein the outer cam race is in a fixed, non-rotating relationship relative to the housing.

8. The driver of claim 1 wherein a cam retainer interface on an outer surface of the outer cam race is held in a fixed, non-rotatable relationship with a complementary cam retainer interface on an inner surface of the proximal housing section.

9. The driver of claim 8 wherein the asymmetrical profile of the cam lobes on the inner race surface of the outer cam race limit rotation of the driver output shaft detachably inserted into the shaft port of the distal housing section to a single direction.

10. The driver of claim 1 wherein the ball cage has a cam assembly bore concentric with the rotation axis of the housing, the cam assembly bore being configured to engage an asymmetric interface of the driver output shaft to prevent rotation of the ball cage of the cam bearing assembly relative to the driver output shaft.

11. The driver of claim 1 wherein a central bushing runs through the inner race, concentric with the rotation axis and slidable over a shank of the driver output shaft.

12. The driver of claim 1 wherein the bearing load assembly comprises a biasing device selected from the group consisting of: a coil spring, a set of Belleville washers, a gradient compression device, a gas piston, and a compression resistant material in mechanical communication with the torque-limiting assembly.

13. The driver of claim 1 wherein the bearing load assembly is in mechanical communication with a thrust bearing assembly biasing against the torque-limiting assembly.

14. The driver of claim 1 further comprising a handle disposed at the drive interface of the proximal housing section.

15. The driver of claim 1 wherein a ball throw distance (Tb) is defined as the distance between the bottom ball detent portion intermediate the opposed ramp portions and the can high-point portion of one of the lobes along a radius of the rotation axis.

16. The driver of claim 1 wherein the torque-limiting assembly is adjustable to selectively transmit a torque (Vr) from the drive interface of the housing to the driver output shaft that is detachably insertable into the shaft port at the distal end of the housing.

17. The driver of claim 1 wherein the outer surface of the inner race forms an angle between the radial vector (Vr) and a ball radius perpendicular to a point of contact of the ball bearing with the outer surface of the inner race, the angle increasing as the inner race is axially displaced in the first direction along the rotation axis as a result of the torque force imparted to the driver.

18. A torque-limiting fastener driver, which comprises:
a) a housing comprising a proximal housing section having a drive end at which a drive interface is disposed, and a distal housing section connected to the proximal housing section by a housing coupling, wherein the distal housing section has a shaft port into which a driver output shaft is insertable to extend along a rotation axis of the fastener driver;
b) a torque-limiting assembly disposed within the housing, the torque-limiting assembly comprising:
  i) a cam bearing assembly comprising at least two ball bearings held in a departured relationship to each other by a ball cage, ii) an outer cam race in which the ball bearings are received, wherein the outer cam race has an inner race surface provided with a plurality of asymmetric cam lobes, each asymmetric cam lobe comprising a cam high point spaced from a bottom ball detent portion intermediate opposed ramp portions of a lesser and a greater pitch, and iii) an inner race comprising a dome shaped portion with an outer surface aligned symmetrically along the rotation axis, iv) wherein the outer cam race contacts each ball bearing received in a lobe at a radial vector (Vr) that is aligned substantially along a radius perpendicular to the rotation axis of the fastener driver, and the outer surface of the inner race forms an angle between the radial vector (Vr) and a ball radius perpendicular to a point of contact of the ball bearing with the outer surface of the inner race, the angle increasing as an axial displacement (Ta) of the inner race increases as a result of a torque force imparted to the driver, c) wherein in a rest position of the driver, the ball bearings reside in the bottom ball detent portion of a first cam lobe of the outer cam race and in contact with the inner race, and d) wherein with the driver output shaft received in the shaft port at the distal housing section, the drive end of the proximal housing section is manipulatable to impart a torque force that causes the inner race to rotate about the rotation axis as the ball bearings contacting the outer cam race at the radial vector move up the lesser pitch ramp of one of the plurality of asymmetric cam lobes while contacting the outer surface of the inner race at a non-radial vector to thereby axially displace the inner race in a first direction along the rotation axis as the angle increases until the ball bearings crest at the cam high point and fall along the greater pitch ramp into the bottom ball detent portion of a next one of the plurality of asymmetric cam lobes with the inner race then moving in a second, opposite direction along the rotation axis back to the rest position.

19. The driver of claim 18 wherein a bearing load assembly provides a bias force (F) against the torque-limiting assembly.

20. A torque-limiting fastener driver, which comprises:
a) a housing comprising a proximal housing section having a drive end at which a drive interface is disposed, and a distal housing section connected to the proximal housing section by a housing coupling, wherein the distal housing section has a shaft port into which a driver output shaft is detachably insertable to extend along a rotation axis of the fastener driver;
b) a torque-limiting assembly disposed within the housing, the torque-limiting assembly comprising:
i) a cam bearing assembly comprising at least two ball bearings held in a departured relationship to each other by a ball cage,
ii) an outer cam race in which the ball bearings are received, wherein the outer cam race, which is in a fixed, non-rotating relationship relative to the housing, has an inner race surface provided with a plurality of repeating asymmetric cam lobes, each asymmetric cam lobe comprising a cam high point spaced from a bottom ball detent portion intermediate opposed ramp portions of a lesser and a greater pitch, and
iii) an inner race comprising a dome shaped portion with an outer surface aligned symmetrically along the rotation axis,
iv) wherein the outer cam race contacts each ball bearing received in a lobe at a radial vector (Vr) that is aligned substantially along a radius perpendicular to the rotation axis of the fastener driver, and the outer surface of the inner race forms an angle between the radial vector (Vr) and a ball radius perpendicular to a point of contact of the ball bearing with the outer surface of the inner race, the angle increasing as an axial displacement (Ta) of the inner race increases as a result of a torque force imparted to the driver,
c) wherein in a rest position of the driver, the ball bearings reside in the bottom ball detent portion of a first cam lobe of the outer cam race and in contact with the inner race, and
d) wherein with the driver output shaft received in the shaft port at the distal housing section, the drive end of the proximal housing section is manipulatable to impart a torque force that causes the inner race to rotate about the rotation axis as the ball bearings contacting the outer cam race at the radial vector move up the lesser pitch ramp of one of the plurality of asymmetric cam lobes while contacting the outer surface of the inner race at a non-radial vector to thereby axially displace the inner race in a first direction along the rotation axis as the angle increases until the ball bearings crest at the cam high point and fall along the greater pitch ramp into the bottom ball detent portion of a next one of the plurality of asymmetric cam lobes with the inner race then moving in a second, opposite direction along the rotation axis back to the rest position.

21. The driver of claim 20 wherein a bearing load assembly provides a bias force (F) against the torque-limiting assembly.

22. The driver of claim 21 wherein the bias force is adjustable to selectively set a maximum amount of torque transmitted via the drive interface to the driver output shaft that is detachably insertable into the shaft port at the distal section of the housing.

23. A torque-limiting fastener driver, which comprises:
a) a housing comprising a proximal housing section having a drive end at which a drive interface is disposed, and a distal housing section connected to the proximal housing section by a housing coupling, wherein the distal housing section has a shaft port into which a driver output shaft is detachably insertable to extend along a rotation axis of the fastener driver;
b) a torque-limiting assembly disposed within the housing, the torque-limiting assembly comprising:
i) a cam bearing assembly comprising at least two ball bearings held in a departured relationship to each other by a ball cage, and
ii) an outer cam race in which the ball bearings are received, wherein the outer cam race has an inner race surface provided with a plurality of repeating asymmetric cam lobes, each asymmetric cam lobe comprising a cam high point spaced from a bottom ball detent portion intermediate opposed ramp portions of a lesser and a greater pitch, and
iii) an inner race comprising a dome-shaped outer surface aligned symmetrically along the rotation axis; and
c) a bearing load assembly providing a bias force (F) against the torque-limiting assembly, wherein the bias force is adjustable to selectively set a maximum amount of torque that is transmittable via the drive interface to the driver output shaft that is detachably insertable into the shaft port at the distal section of the housing, d) wherein in a rest position of the driver, the ball bearings reside in the bottom ball detent portion of a first cam lobe of the outer cam race and in contact with the inner race, and e) wherein with the driver output shaft received in the shaft port at the distal housing section, the drive end of the proximal housing section is manipulatable to impart a torque force that causes the inner race to rotate about the rotation axis as the ball bearings contacting the outer cam race at the radial vector (Vr) aligned substantially along a radius perpendicular to the rotation axis of the fastener driver to move up the lesser pitch ramp of one of the plurality of asymmetric cam lobes while contacting the outer surface of the inner race at a non-radial vector to thereby axially displace the inner race in a first direction along the rotation axis until the ball bearings crest at the cam high point and fall along the greater pitch ramp into the bottom ball detent portion of a next one of the plurality of asymmetric cam lobes with the inner race then moving in a second, opposite direction along the rotation axis back to the rest position.

* * * * *

UNITED STATES PATENT AND TRADEMARK OFFICE
CERTIFICATE OF CORRECTION

| | | |
|---|---|---|
| PATENT NO. | : 8,475,466 B2 | Page 1 of 1 |
| APPLICATION NO. | : 11/958447 | |
| DATED | : July 2, 2013 | |
| INVENTOR(S) | : Fabrice Chenaux | |

It is certified that error appears in the above-identified patent and that said Letters Patent is hereby corrected as shown below:

On the title page item 75 (Inventor, line 1) delete "West Chester" and insert --Exton--

In the Claims

Column 10, line 40 (Claim 15, line 3) delete "can" and insert --cam--

Column 13, line 10 (Claim 23, line 10) delete "at the" and insert --at a--

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,475,466 B2 | Page 1 of 1 |
| APPLICATION NO. | : 11/958447 | |
| DATED | : July 2, 2013 | |
| INVENTOR(S) | : Chenaux | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 896 days.

Signed and Sealed this
Nineteenth Day of April, 2016

Michelle K. Lee
*Director of the United States Patent and Trademark Office*